(12) United States Patent
Knight

(10) Patent No.: US 8,618,118 B2
(45) Date of Patent: Dec. 31, 2013

(54) REMEDY FOR MIGRAINE HEADACHE

(76) Inventor: Joseph Robert Knight, Oak Park, CA (US)

(*) Notice: Subject to any disclaimer, the term of this patent is extended or adjusted under 35 U.S.C. 154(b) by 0 days.

(21) Appl. No.: 13/359,393

(22) Filed: Jan. 26, 2012

(65) Prior Publication Data

US 2013/0143903 A1  Jun. 6, 2013

Related U.S. Application Data

(60) Provisional application No. 61/436,370, filed on Jan. 26, 2011.

(51) Int. Cl.
*A01N 43/90* (2006.01)
*A61K 31/522* (2006.01)

(52) U.S. Cl.
USPC ..................................... 514/263.34

(58) Field of Classification Search
None
See application file for complete search history.

(56) References Cited

U.S. PATENT DOCUMENTS

| | | | |
|---|---|---|---|
| 4,639,465 A | 1/1987 | Pollack | |
| 4,665,069 A | 5/1987 | Rosenberg | |
| 4,870,097 A | 9/1989 | Makovec | |
| 4,962,121 A * | 10/1990 | Hamberger et al. | 514/419 |
| 5,326,569 A * | 7/1994 | Acosta et al. | 424/440 |
| 6,268,386 B1 | 7/2001 | Thompson | |
| 2002/0187958 A1* | 12/2002 | Horrobin et al. | 514/52 |
| 2006/0105023 A1* | 5/2006 | Knight | 424/439 |
| 2007/0043120 A1 | 2/2007 | Beyreuther et al. | |
| 2008/0139510 A1 | 6/2008 | Rose | |

FOREIGN PATENT DOCUMENTS

| | | |
|---|---|---|
| DE | 60113704 T2 | 6/2006 |
| EP | 1637185 | 3/2006 |
| WO | WO 2008142392 A1 * | 11/2008 |
| WO | WO2010112942 | 7/2010 |

* cited by examiner

*Primary Examiner* — Robert T Crow
*Assistant Examiner* — Doan Phan
(74) *Attorney, Agent, or Firm* — Patent Law & Venture Group; Gene Scott

(57) ABSTRACT

A medication formulation and method of use for treating migraine having a combination of active ingredients including: nicotine, phenylalanine, tyrosine, and caffeine in an aqueous solution.

10 Claims, 5 Drawing Sheets

NICO WORLDWIDE, LLC

Name: ( ) Date of Study: ( 10/20/11)

Log on Name: ( cathyevans514@yahoo.com) Password: ( catann5 )

MICROTINE'S MIGRAINE SURVEY

PART II

This will be the ongoing survey form being utilized for the length of the study
This form must be filled out every time you suffer a migraine experience to maintain
current in the study and to assure being kept in the study.

If one bottle of Microtine™ does not provide relief within ten minutes, please take a second.

1. How severe is your current migraine?
   With 1 being mildest to 10 being most severe – put an x by the appropriate number
   1 ( ) 2 ( ) 3 ( ) 4 ( ) 5 ( x ) 6 ( ) 7 ( ) 8 ( ) 9 ( ) 10 ( )

2. How often do you currently have migraines?
   a. daily ( )
   b. weekly ( )
   c. 2 a week ( x )
   d. monthly ( )
   e. 2 a month ( )
   f. every 3 months ( )
   g. every 6 months ( )
   h. 1 a year ( )

3. Are you still using your OTC/ Prescription migraine medication?
   Yes ( x )
   No ( )

4. Are you using Microtine™?
   Yes ( x )
   No ( )

5. For relief, was a second bottle of Microtine™ needed 10 minutes after the first?
   Yes ( x )
   No ( )

FIG. 3A

6. After taking Microtine – in 15 minutes intervals – with 1 being mildest to 10 being most severe –

Rate Your Pain

|  | 1 | 2 | 3 | 4 | 5 | 6 | 7 | 8 | 9 | 10 |
|---|---|---|---|---|---|---|---|---|---|---|
| 15 minutes |  |  |  |  | x |  |  |  |  |  |
| 30 minutes |  |  |  | x |  |  |  |  |  |  |
| 45 minutes |  |  |  |  |  |  |  |  |  |  |
| 60 minutes |  |  | x |  |  |  |  |  |  |  |
| 1 hour and 15 minutes |  | x |  |  |  |  |  |  |  |  |
| 1 hour and 30 minutes |  | x |  |  |  |  |  |  |  |  |
| 1 hour and 45 minutes | x |  |  |  |  |  |  |  |  |  |
| Two hours | x |  |  |  |  |  |  |  |  |  |

7. How long did the Migraine last?

a. 5 – 10 minutes ( )
   b. 15 – 25 minutes ( )
   c. 30 – 45 minutes ( )
   d. 60 - minutes ( )
   e. 1 1/2 hours ( )
   f. 3 - hours ( x )
   g. 24 - hours ( )
   h. other ( )(explain)

8. How long does the entire migraine experience last?

From the first warning until you are completely over the migraine pain/hangover and feeling back to normal )

a. 30 – 60 minutes ( )
   b. 1 ½ hour ( )
   c. 2 - 4 hours ( x )
   d. 4 - 8 hours ( )
   e. 12 hours ( )
   f. 24 hours ( )
   g. 36 hours ( )
   h. 48 hours ( )
   i. 72 hours ( )
   j. How long (explain)

9. Did you experience any side effects from Microtine™?
   No ( x )

FIG. 3B

If you answer no – please skip question 10

10. In the space provided, please describe the side effects and duration you experienced from Microtine™?

11. With 1 being inferior to 10 being superior, please compare Microtine™ to your previous Medication
    1( ) 2( ) 3( ) 4( ) 5( ) 6( ) 7( ) 8(x) 9( ) 10( )

12. In the space provided below, compare Microtine™ to the other migraine medications you have been taking. Please be specific.

I just usually take aspirin free. It only works when I have an aura first and can "catch it" before the actual pain starts. Microtine may work right away for me or it might take awhile. It does dull the pain & the migraine does go away much faster than it probably would have.

13. If you are not going to stay with the study, please explain?

If you have any questions call Alex Slabo 1-805-278-9744
or at email migrainestudy@nicoworldwide.com

FIG. 3C

REMEDY FOR MIGRAINE HEADACHE

CROSS-REFERENCE TO RELATED APPLICATIONS

This application contains subject matter identical or similar to that of Provisional Patent Application 61/436,3704, filed on Jan. 26, 2011 and claims international date priority therefrom. The subject matter of application 61/436,3704 is hereby incorporated hereinto in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND

The present formulation relates to the field of pharmaceutical treatments for pain and in particular to severe headache such is produced by a migraine episode. The term "migraine" is used herein to mean both common migraine headache and classic migraine headache, and also any human severe headache condition although some such conditions may be referred to by other terminology in the field of medicine or by the general public.

Migraine is a painful, sometimes debilitating disorder, which is frequently associated with various neurological symptoms. Its prevalence in the population is higher than that of any other neurological disorder, thus the burden of this disease on society is considerable. Although the introduction of triptans nearly two decades ago revolutionized the treatment of the disease there is still a strong need for a more effective pharmacology. Formerly, migraine therapy primarily aimed at treating the pathological alterations of meningeal blood vessels that are thought to directly initiate migraine. Now, it has been increasingly recognized that abnormal neural function may be a greater cause in the development of the disease and also in triggering an episode. Migraine is now believed to be associated with an increased neuronal excitability and episodes of cortical spreading depression.

A migraine may include intense throbbing pain, nausea, and sensitivity to light (aura) and sound. The condition is relatively common in adults aged 25 through 55 and is more prevalent in women. Triptans have been used in medications for the treatment of migraine. Included are: Sumatriptan®, Rizatrptan®, Naratriptan®, Zolmitriptan®, Eletriptan®, Almotriptan®, Frovatriptan®, and Avitriptan®. While effective in treating the occurrence of migraine, they have not proven effective for preventive treatment and do not provide long term relief. They act by temporarily constricting the brain's blood vessels relieving swelling. The etiology of migraine is not yet fully understood although a body of scientific research shows that certain biochemical mechanisms are repeatedly found in the pathophysiology of migraine including migraine with and also without aura.

Homeopathic remedies have included preparations having magnesium, ginger, ginkgo-biloba, feverfew, and melatonin, to name only a few. The amino acid tryptophan, in tablet or capsule form, is a commonly accepted method for the administration of tryptophan, and remains an available and effective way to elevate the level of serotonin within the brain. Also known is the prophylactic use of tryptophan in treating stress. In the treatment of migraine, however, clinical evidence shows that it is usually only moderately effective. Tests indicate that the primary benefits of tryptophan lie in its routine, daily use as a preventive. It has been found to minimize migraine frequency and in some cases, also headache intensity and duration. Repeatedly however, tryptophan has been shown to be ineffective in aborting or significantly mitigating pain after the onset of a migraine episode.

Therefore, a medication is needed that can be taken orally, and which allows accelerated delivery of medication to the central nervous system so as to reduce or eliminate the pain associated with migraine. An effective remedy, described herein, has been found to be effective in treating migraine headache from onset to completion.

SUMMARY AND OBJECTIVES

It is an object of this disclosure to present a novel medication and delivery approach for the treatment of migraine. Another objective is to provide a form of the medication that is able to be taken orally. Another objective is to provide such a remedy that acts quickly upon the onset of migraine. A further objective is to provide such a remedy that is safe, consistent, and repeatable.

The details of one or more embodiments of these concepts are set forth in the accompanying drawings and the description below. Other features, objects, and advantages of these concepts will be apparent from the description and drawing figures, and from the claims.

BRIEF DESCRIPTION OF THE SEVERAL VIEWS OF THE DRAWING

FIG. 3A is an example filled-out first data sheet of a migraine headache survey by a subject of the clinical study.

FIG. 3B is an example filled-out second sheet of the clinical study; and

FIG. 3C is an example filled-out third sheet of the clinical study.

DETAILED DESCRIPTION

The presently described remedy includes a medication formulation and a proposed delivery method for treating migraine. The formulation may include active ingredients: nicotine, tryptophan, phenylalanine, tyrosine, and caffeine, incorporated into a two fluid ounce aqueous solution to be consumed as a beverage. Other ingredients may be added as well such as preservatives, flavorings, and non-essential amino acids. The liquid portion of the solution is not active and may be water or almost any other fluid.

Figure 1:
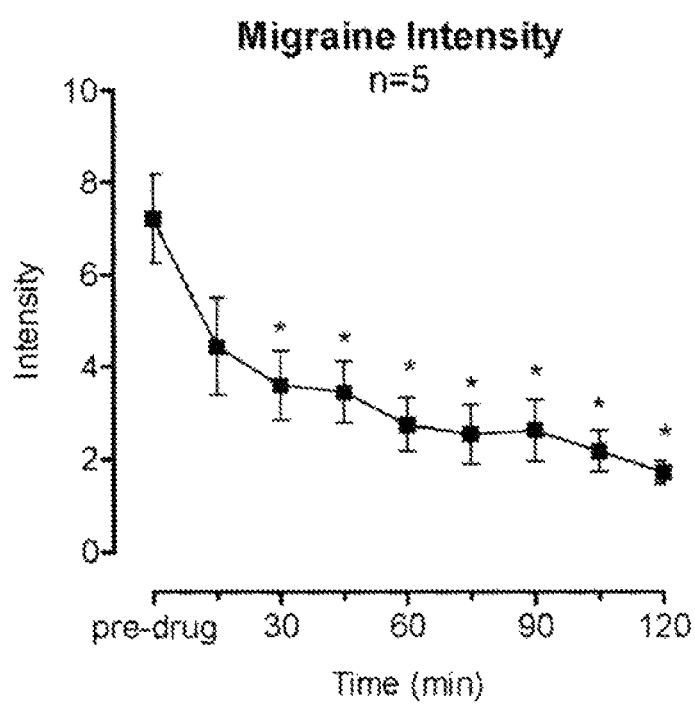
FIG. 1 is an example graph showing migraine pain intensity plotted against time, with each data point representing the mean of five subjects.
Figure 2:
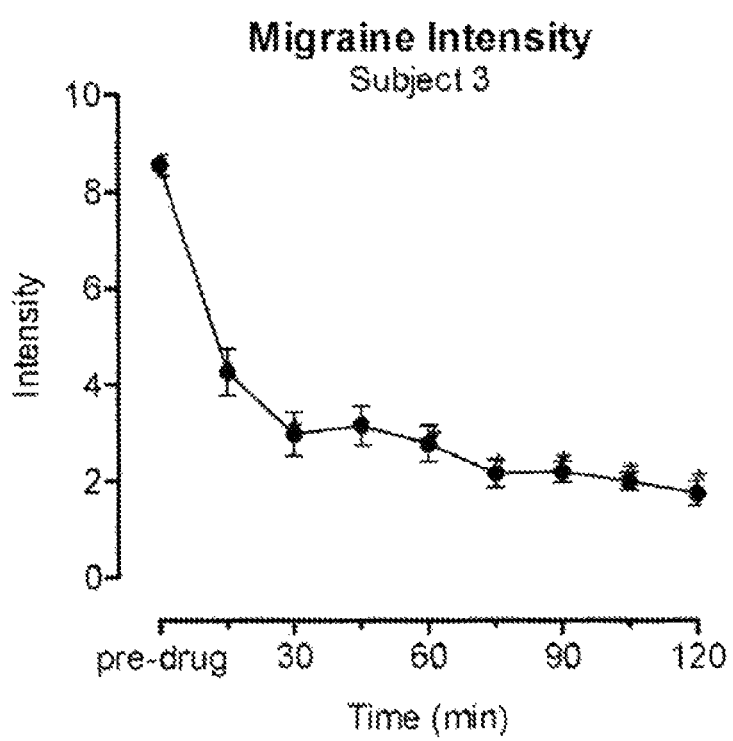
FIG. 2 is an example graph showing migraine pain intensity plotted against time for a single subject.

A well-controlled clinical study has been carried out by Nico World Wide, Inc. of Oxnard, Calif. This study is continuing at this time. This application is based upon initial results using five subjects suffering from migraine episodes. These subjects drank the beverage, referred to by its trademark, Microtine™ as prepared in the study, at migraine episode onset. The subjects were then asked to assess their pain level on a scale of 1-10, is with 10 being the most pain they have ever experienced in migraine episodes. This assessment was done at 15 minute intervals over a test period of two hours during each migraine episode. FIG. 1 shows migraine pain intensity plotted against time, with each data point representing the mean of five subjects, and also shows plus/minus standard error of the mean. No adverse side-effects were reported by the subjects during the study, FIG. 2 again shows migraine pain intensity plotted against time for a single subject. The graph shows the average pain intensity of 11 migraine episodes in 15 minute intervals experienced over a two month period.

These data show a significant decrease in the average pain intensity over the test periods of 120 minutes. Additionally, within a single subject it has been shown that there is no loss of effectiveness after repeated exposure. At the onset of migraine, the average pain intensity was found to be 8.6 prior to ingesting the beverage. Fifteen minutes after ingestion of the beverage pain intensity was shown to have dropped to an average level of 4.3; a significant improvement. The beverage significantly reduced the pain intensity for the remainder of each of the tested episodes, with an average intensity of 1.8 at the end of the tests. These data provide evidence of meaningful pain relief to migraine sufferers and suggests that there is no loss of effectiveness after repeated exposure and that the beverage provides quick relief.

The active ingredients in the beverage may be formulated in the following weight percentages:

| | |
|---|---|
| nicotine | 0.11% |
| tryptophan | 18.1% |
| phenylalanine | 9.0% |
| tyrosine | 27.1% |
| caffeine | 38.4% |

It has been found that the five active ingredients are effective in combinations within the following ranges:

| | |
|---|---|
| nicotine | 0.11 to 2.0% |
| tryptophan | 15.0 to 30.0% |
| phenylalanine | 5.0 to 15.0% |
| tyrosine | 20.0 to 30.0% |
| caffeine | 35.0 to 50.0% |

Nicotine acts as an anti-inflammatory agent in multiple cell types and may be beneficial in central nervous system disorders associated with inflammatory responses such as Alzheimer's and Parkinson's disease. As migraine is also believed to be the result of inflammation of blood vessels in the brain, it is hypothesized that nicotine may alleviate migraine pain through an anti-inflammatory mechanism.

Tryptophan is known to treat stress which is an environmental trigger for migraine and, as mentioned above, a low serotonin level may be a factor in developing migraine. Thus the combination of these two chemicals act to provide an anti-inflammatory effect and reduce stress, both mechanisms which may mitigate migraine pain.

The formulation may also contain non-essential amino acids such as serine, aspartic acid, and glutamic acid which act as excitatory neurotransmitters to the central nervous system including, the brain and the spinal cord.

The formulation may theoretically be inhaled, ingested, injected, received trans dermally or by any other transport means. Ingestion by drinking the beverage has been shown to be effective.

As stated above, the medication formulation for treating migraine comprises an aqueous solution, the beverage, containing active ingredients including an effective amount of: nicotine, tryptophan, phenylalanine, tyrosine and caffeine, wherein the nicotine comprises approximately between 0.11-2.0%. However, it has been found that the formulation of an effective amount of nicotine and tryptophan alone provides many of the benefits of the full formulation. Adding an effective amount of phenylalanine improves results for some subjects. Further adding an effective amount of tyrosine improves results for further subjects, and further adding an effective amount of caffeine improves results even further for some subjects. In the formulation the solution may have 0.222 mg nicotine, 40 mg tryptophan, 20 mg phenylalanine, 60 mg tyrosine, and 85 mg caffeine in two liquid ounces of water or equivalent liquid. Additionally, it has been found that a non-essential amino acid for example: serine, aspartic acid, and glutamic acid may have beneficial results.

Embodiments of the subject apparatus and method have been described herein. Nevertheless, it will be understood that various modifications may be made without departing from the spirit and understanding of this disclosure. Accordingly, other embodiments and approaches are within the scope of the following claims.

What is claimed is:

1. A medication formulation for treating migraine comprising an aqueous solution containing active ingredients including an effective amount of: nicotine, tryptophan, phenylalanine, tyrosine and caffeine, wherein the nicotine comprises approximately 0.222 mg.

2. A medication formulation for treating migraine comprising an aqueous solution containing active ingredients including approximately: 0.222 mg nicotine, 40 mg tryptophan, 20 mg phenylalanine, 60 mg tyrosine, and 85 mg caffeine in approximately two liquid ounces of water.

3. The medication formulation of claim 1 wherein the nicotine represents about 0.11% by weight of the active ingredients.

4. The medication formulation of claim 1, wherein the tryptophan represents between 15% and 30% by weight of the active ingredients.

5. The medication formulation of claim 1, wherein the phenylalanine represents between 5% and 15% by weight of the active ingredients.

6. The medication formulation of claim 1, wherein the tyrosine represents between 20% and 30% by weight of the active ingredients.

7. The medication formulation of claim 1, wherein the caffeine represents between 35% and 50% by weight of the active ingredients.

8. A medication formulation for treating migraine comprising an aqueous solution containing active ingredients including by weight approximately: nicotine 0.1%, tryptophan 18.1%, phenylalanine 9.0%, tyrosine 27.1%, and caffeine 38.4%.

9. The medication formulation of claim 8 further including at least one non-essential amino acid.

10. The medication formulation of claim 9 wherein the non-essential amino acid is at least one of: serine, aspartic acid, and glutamic acid.

* * * * *